(12) United States Patent
Kumakhov et al.

(10) Patent No.: US 7,116,753 B2
(45) Date of Patent: Oct. 3, 2006

(54) METHOD FOR DETERMINATION OF ELASTIC STRAINS PRESENT IN SINGLE-CRYSTAL WAFERS AND DEVICE FOR ITS REALIZATION

(75) Inventors: Muradin A. Kumakhov, Moscow (RU); Nariman S. Ibraimov, Moscow (RU); Alexander V. Lyuttsau, Moscow (RU); Svetlana V. Nikitina, Moscow (RU); Alexander V. Kotelkin, Moscow (RU); Alexander D. Zvonkov, Moscow (RU)

(73) Assignee: Institute for Roentgen Optics, Moscow (RU)

( * ) Notice: Subject to any disclaimer, the term of this patent is extended or adjusted under 35 U.S.C. 154(b) by 0 days.

(21) Appl. No.: 10/878,189

(22) Filed: Jun. 29, 2004

(65) Prior Publication Data

US 2005/0041777 A1    Feb. 24, 2005

(30) Foreign Application Priority Data

Aug. 22, 2003    (RU) ............... 2003125781

(51) Int. Cl.
G01N 23/207    (2006.01)
G01N 23/20    (2006.01)

(52) U.S. Cl. ......................... 378/73; 378/71
(58) Field of Classification Search ............ 378/71, 378/72, 73, 76
See application file for complete search history.

(56) References Cited

U.S. PATENT DOCUMENTS 4,078,175 A * 3/1978 Fletcher et al. ............... 378/72
4,916,720 A * 4/1990 Yamamoto et al. ........... 378/72
5,192,869 A    3/1993 Kumakhov
6,058,160 A * 5/2000 Kurtz ............................ 378/72

OTHER PUBLICATIONS

Cargill III, G.S., "Novel applications of X-ray analysis to microelectronic materials and devices", Solid-State Electronics, Aug. 2002, vol. 46, Issue 8, pp. 1139-1143.*

Kawano, et al., "Highly sensitive and tunable detection of far-infrared radiation by quantum Hall devices," Journal of Applied Physics, Apr. 1, 2001, pp. 4037-4048, vol. 89, No. 7, American Institute of Physics, US.

Brümmer, V. O., "About the simultaneous generation of the roentgen-interference and of the roentgen-silhouette of crystals," Zeitschrift für Naturforschung, 15a, Jun. 12, 1960, pp. 875-879, Halle University, Institute of Experimental Physics, Germany.

* cited by examiner

*Primary Examiner*—Edward J. Glick
*Assistant Examiner*—Chih-Cheng Glen Kao
(74) *Attorney, Agent, or Firm*—McDermott Will & Emery LLP

(57) ABSTRACT

Action on the tested wafer 1 is rendered with X-ray beam 3 converging in a point located inside the wafer or under it. Determination of relative position of the interference maxima is performed for diffraction reflections from crystallographic planes having the form of {nKK}, where n is equal to H, K or L and differs for distinct crystallographic planes.

Means 11 for beam shaping creates beam 3 simultaneously acting on multiple crystallographic planes. Detectors 13 receive diffracted radiation in the whole angular range containing the interference maxima corresponding to the reflections from the irradiated planes.

4 Claims, 5 Drawing Sheets

METHOD FOR DETERMINATION OF ELASTIC STRAINS PRESENT IN SINGLE-CRYSTAL WAFERS AND DEVICE FOR ITS REALIZATION

CROSS-REFERENCE TO RELATED APPLICATIONS

Not Applicable

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC

Not Applicable.

BACKGROUND OF THE INVENTION

1. Field of the Invention

The inventions proposed are related to X-ray means for detecting of the elastic strains present in single-crystal wafers and are intended, in particular, for use in monitoring of the manufacturing process of printed-circuit substrates in microelectronics.

2. Description of Related Art

A method is known for detection of elastic strains present in a single crystal, is based on its interaction with monochromatic infrared radiation (see Y. Kawano et al., Infra Red System GaAs/AlGaAs., J. Appl. Phys. 2001, 89, p. 4037 [1]). At the sites of disturbances of periodicity and orientation of crystal lattice the interference maxima of infrared radiation are observed, and registered by semiconductor sensors.

In single-crystal materials with metallic interatomic bonds (germanium, silicon, arsenic, and others), transmission over them of thermal vibrations results in broadening of said maxima and rising of background level up to their merging. This makes the usage of said method in manufacturing wide assortment of single-crystal wafers impossible.

Also known is X-ray method for detection of elastic strains located in single-crystal wafers (see O. Brümmer. Zeitschrift für Naturforschungen, 15A, S.875, 1960 [2]).

This method is based on detection of crystallographic planes departures from relative orientation.

Surface of single-crystal wafer is illuminated with widely diverging X-ray beam. Diffracted radiation is registered with a flat X-ray film. The recorded diffraction of the interference pattern is compared with a reference pattern obtained for reference standard single-crystal wafer, and a conclusion about presence or absence of elastic strains in single-crystal wafer inspected is reached by the degree of their divergence. Angular divergence of illuminating beam is adjusted so as to ensure fulfillment of diffraction conditions for two or three sets of crystallographic planes. For the most of widely used materials of single-crystal wafers said angular divergence of illuminating beam can reached of 30–40°.

Using of a beam having such a large divergence implies large illuminated surface area of single-crystal wafer participating in diffraction and, as a consequence, results in generation of averaged interference pattern, induced by diffraction in different geometric points of a surface. Therefore, unambiguous interpretation of interference pattern of diffraction registered on the film is made difficult. Because of this, high probability of erroneous results of the control. Besides, photographic method of registration used requires large exposure times (several hours) as well as some satisfactions simultaneously the requirements to resolution and contrast. This constitutes the principal obstacle to establishing complete control in flow-line production, thus inducing forcedly random testing of a small number of wafers.

Method and device known from [2] are the most close ones to those proposed.

BRIEF SUMMARY OF THE INVENTION

The inventions proposed are intended to ensure technical result comprising increase in control reliability and provision of express test, which creates possibility of complete control of single-crystal wafers at different stages of manufacturing process. Below, in disclosure of the inventions proposed and their specific embodiments, other kinds of technical result achieved will be also revealed.

In the method proposed, similar to the most close one known from [2], single-crystal wafer inspected is exposed to X-ray beam, interference diffraction pattern is registered, and relative position of interference maxima are determined, by which presence of elastic strains is ascertained.

To achieve technical results specified, in the method proposed, as distinct from the most close one known, single-crystal wafer inspected is irradiated with converging X-ray beam that having point of rays interception located or inside the body of single-crystal wafer inspected or on the opposite side to that said converging X-ray beam falls upon. At that, determination of relative position of interference maxima is performed for diffraction reflections from multiple crystallographic planes of the type nKK, where n may take on values H, K or L, distinct for different planes selected. Determination of relative position of the interference maxima is performed by means of one or numbers position-sensitive X-ray detectors.

The formation of converging X-ray beam is accomplished preferably by means of Kumakhov focusing X-ray lens (see, for example, U.S. Pat. No. 5,192,869, publ. Sep. 3, 1993 [3]).

The device proposed, in common with the most close one known from [2], comprises means for positioning the single-crystal wafer inspected and X-ray emitter equipped with beam-shaping means for said radiation. Shaped beam is oriented so as to provide for X-radiation acting on the single-crystal wafer inspected, placed in the positioning means. The device comprises also means for registration of interference pattern of diffraction.

To achieve technical results specified, in the device proposed, as distinct from the most close one known, the beam-shaping means for X-radiation acting on single-crystal wafer inspected are made with possibility of converging beam formation. Point of rays intersection in said beam is situated inside the single-crystal wafer inspected or on the side opposite to that onto which said beam falls. Besides, X-ray beam-shaping means are made with possibility to provide for simultaneous diffraction for multiple crystallographic planes. In this case, means for registration of interference diffraction pattern comprise one or number of position-sensitive X-ray detectors, mounted with possibility of diffracted radiation reception in full angular range containing interference maxima corresponding to reflections from crystallographic planes of material of the single-crystal wafer inspected, having the form of nKK, where n equals to H, K or L and differs for distinct crystallographic planes.

Means for converging X-ray beam shaping are made preferably in the form of X-ray focusing lens (Kumakhov lens [3]).

Employment in the method proposed of converging X-ray beam with rays intersecting in a point situated within the single-crystal wafer inspected or on the side opposite to that onto which said beam falls and use in the device proposed of the means for shaping said beam is required to ensure locality of the action. This allows to eliminate formation of an averaged interference diffraction pattern and to perform scanning of single-crystal wafer surface in order to find the distribution of elastic strains.

Employment in said method and in operating the device proposed of reflections from crystallographic planes in the form of nKK, where n may correspond to H, K or L, is necessary for simultaneous coming of said planes into reflecting position, and provides for alignment of their common plane of normals with diffraction plane. This, in its turn, allows to control changes in diffraction angles for sets of crystallographic planes, consecutively inclined at ever increasing angle (with increasing index n) to the surface of single-crystal wafer. In the presence of elastic stresses in single-crystal wafer, effect of diffraction planes slope relative to the surface on change of diffraction angle is given by a known relationship, thus allowing to level of elastic strains.

Use in the method and device proposed of position-sensitive X-ray detectors for registration of interference pattern of diffraction ensures high accuracy and express quality of the test, possibility of interfacing with fast computing means for automated processing of information contained in output detector signals and displaying its results.

BRIEF DESCRIPTION OF THE SEVERAL VIEWS OF THE DRAWINGS

Method and device proposed are illustrated with drawings, which show.

DETAILED DESCRIPTION OF THE INVENTION

Figure 1:
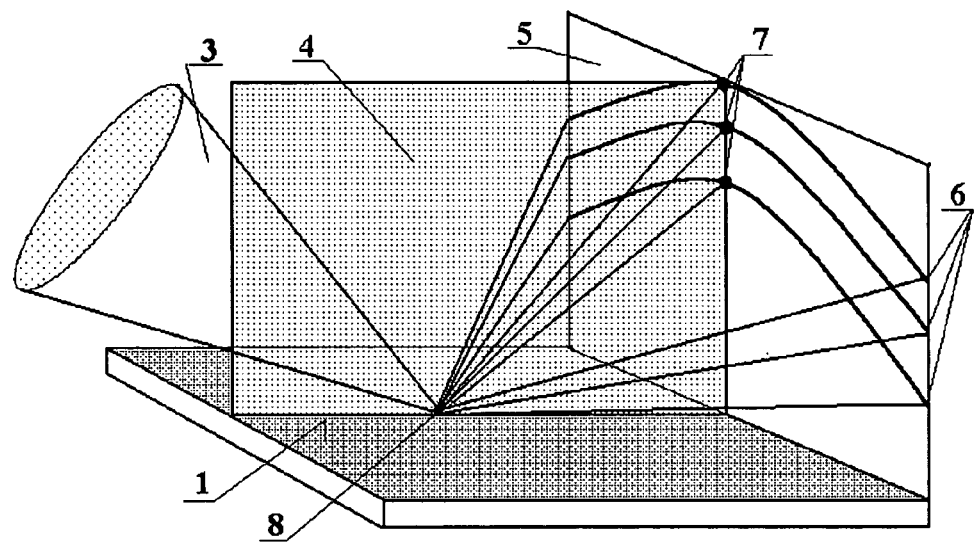
in FIG. 1—schematic representation of diffraction pattern formation.

In the method proposed (see FIG. 1), single-crystal wafer 1 inspected is irradiated upon with a converging X-ray beam 3 and interference diffraction pattern is registered by position-sensitive detector (or multiple position-sensitive detectors). Position-sensitive detectors are arranged in such a way that their windows would lie in the plane 5, perpendicular to the surface of single-crystal wafer 1. Besides, position-sensitive detectors should be arranged so that expected positions of interference maxima 7 for material of wafers inspected with allowances made for their possible alteration due to elastic strains present would fall within boundaries of their windows. Number of position-sensitive detectors utilized would depend on window dimensions of specific position-sensitive detectors available to researcher. Given a position-sensitive detector with extended window, for example, curved on circular arc corresponding to a large angle, one such detector may suffice. It is required that the single or multiple detectors would ensure reception of diffracted radiation in angular range comprising all interference maxima for selected system of crystallographic planes.

Interference maxima are situated on intersection of one of diffraction planes 4 (normal to the surface of inspected single-crystal wafer 1) with traces of diffraction cones 6 intersection with detection plane 5. Relative position of said maxima is determined with the help of single or multiple position-sensitive detectors and used to judge the presence of elastic strains in single-crystal wafer inspected.

The single-crystal wafer inspected is acted upon with a converging X-ray beam 3. Point of rays intersection of said beam should be located inside the single-crystal wafer 1 tested or on the side opposite to that onto which falls said converging X-ray beam 3 (in case of horizontal position of wafer 1 and beam 3 incident from above, as shown in FIG. 1—inside or under the wafer 1). Converging X-ray beam 3 may be obtained by making use of X-ray optical system having curved single crystals, multilayer nanocoatings or, the most efficiently, utilizing polycapillary optics based on the principle of total external reflection of X-ray radiation (Kumakhov X-ray focusing lens [3]).

Figure 2:
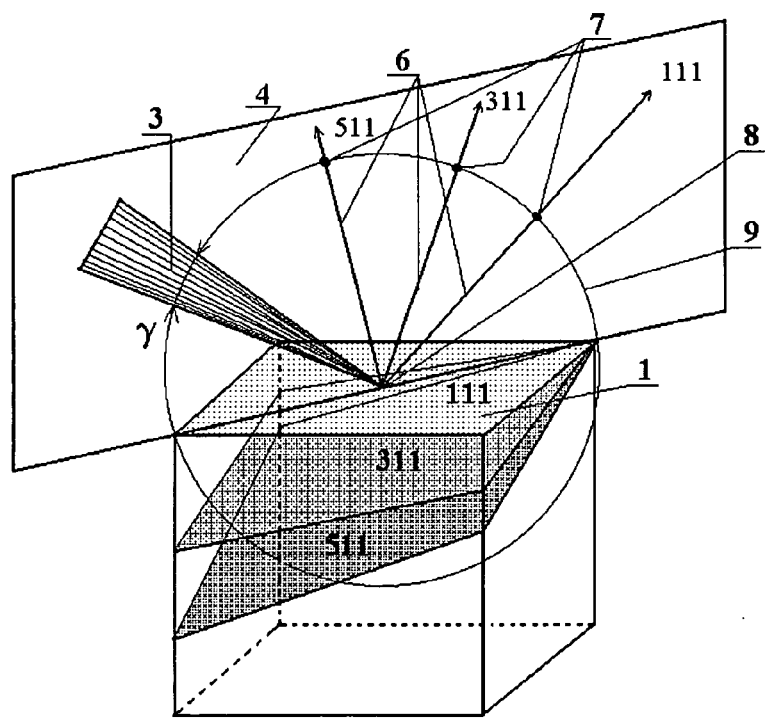
in FIG. 2—simultaneous reflections by multiple crystallographic planes.

The existence in any single-crystal wafer of crystallographic planes with two last like indices, having the form of nKK, where n may assume values of H, K or L (non-coinciding for different planes), results in following. On bringing one of such planes into position parallel to the surface of single-crystal wafer tested (so that diffraction plane, orthogonal to this surface, would coincide with crystallographic plane 0KK, perpendicular to planes nKK), simultaneous diffraction takes place from those of planes nKK, which will find in converging X-ray cone 3 a ray having angle of incidence satisfying equation 2d sin θ=nλ, wherein d denotes interplanar spacing for reflecting set of planes, λ is a wavelength of incident X-ray radiation, n is order of reflection, and θ denotes diffraction angle. In FIG. 2, plane 0KK, coinciding with the diffraction plane, is designated by number 4 and is a diagonal plane of a cube. By the way of example, planes 111, 311, and 511 are chosen. Planes 111 and 511 in manufacture of silicon single-crystal wafers, depending on the objective, are the basal ones, that is, are brought into position parallel to the surface of single-crystal wafer. Most often, single-crystal silicon wafers are manufactured with basal plane 111, and therefore this particular case is considered in FIG. 2 and hereinafter, although all reasoning remains true also for the case of basal plane 511.

The converging X-ray beam 3 with convergence angle γ, shaped by X-ray optical system (any of those specified above) (FIG. 2), irradiated very small part of the surface—irradiation zone 8 of the single-crystal wafer 1. In accordance with abovementioned basic diffraction equation, each plane (111, 311, 511) <<chooses>> from the total number of X-rays in the converging beam 3 that incident at a certain angle, suitable for the fulfillment of diffraction condition. If convergence angle γ of the beam 3 is sufficient to include such rays for all the planes specified, then each of them gives reflection 6 at a diffraction angle to that crystallographic plane. By drawing in plane 4 a circumference 9 with its center at irradiation zone 8 of the single-crystal wafer 1, position-sensitive detector (detectors) may be arranged in localities 7 equidistant from irradiation zone for simultaneous fixation of total interference diffraction pattern in plane 4.

Figure 3:
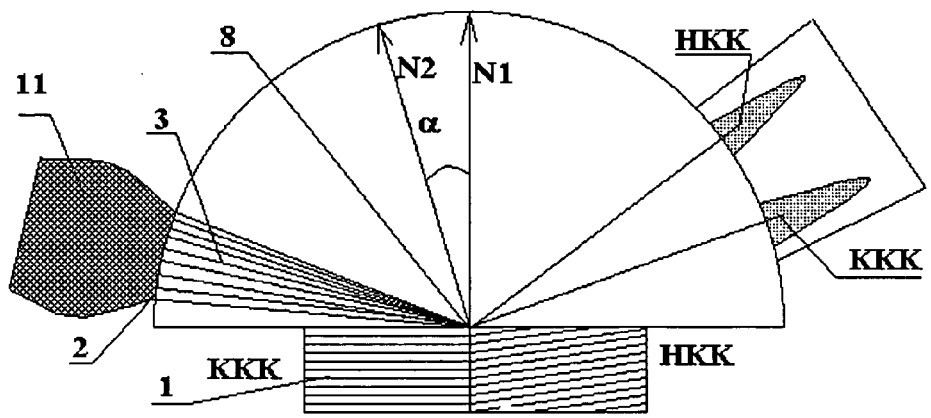
in FIG. 3—differences in angular positions of normals to planes and angular positions of interference reflections for different reflecting planes.

With angle between crystallographic planes KKK and HKK let us designated α (see FIG. 3), for cubic lattice in the general case an angle between planes with indices $h_1 \, k_1 \, l_1$ and $h_2 \, k_2 \, l_2$ may be found by formula:

$$\cos\alpha = \frac{h_1 h_2 + k_1 k_2 + l_1 l_2}{\sqrt{h_1^2 + k_1^2 + l_1^2} \cdot \sqrt{h_2^2 + k_2^2 + l_2^2}}.$$

This is an angle between normals $N_1$ and $N_2$ to planes HKK and KKK (FIG. 3); however, it is by no means equal to angular distance between diffraction interference maxima from planes KKK and HKK, which further depends on interplanar spacing d, different for planes KKK and HKK. Therefore, converging beam 3 shaped by X-ray lens 11, incident to irradiation zone 8 on the surface of single-crystal wafer 1 having basal plane KKK, and comprising a ray incident to the planes system HKK at a diffraction angle to these planes, will be deflected at a different angle from that in planes system KKK, conventionally rotated by angle α and brought into position HKK.

Figure 4:
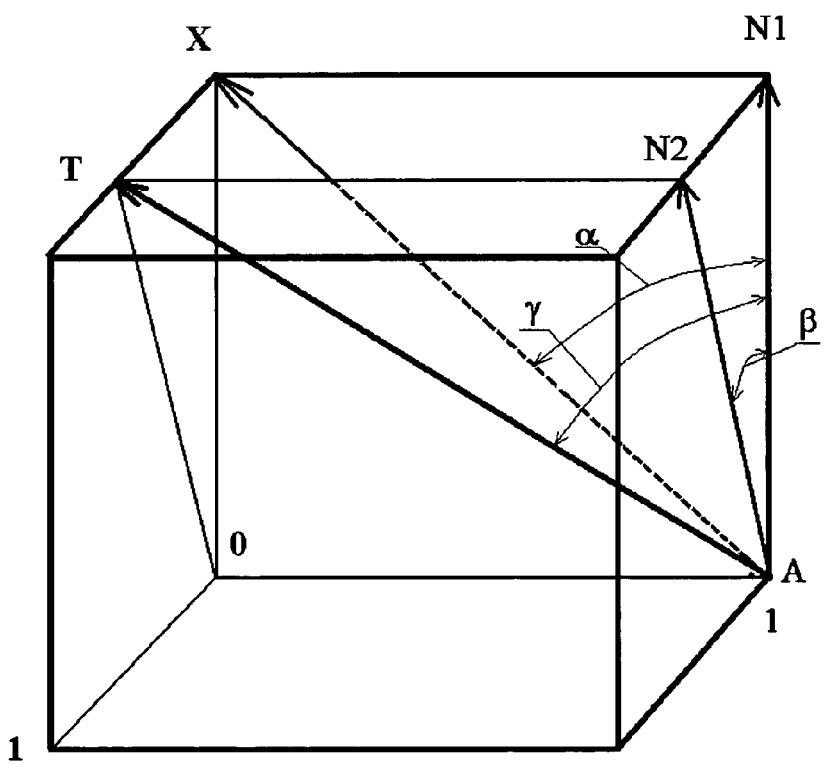
in FIG. 4—geometrical relationships for calculation of angular positions of the normal to the reflecting plane with indices nKK.

In the general case, one should proceed from trigonometric relationships illustrated in FIG. 4.

This drawing shows unit cube, whose orientation relative to surface in ideal single crystal depends on coordinate system. Let us denote inclination angle of the normal to reflecting planes nonparallel to the surface as α, that is, α is an angle between normals $AN_1$ and AX to the planes involved. In this case, plane $AN_1X$ is a diffraction plane. If, due to elastic strains in crystal lattice of the single-crystal wafer, plane $AN_1X$ is inclined by angle β relative to normal $AN_1$, i.e. switches into position $AN_2T$, and correspondingly, direction AX becomes direction AT, then for an angle γ between new normal AT to the plane considered and normal $AN_1$ following formula may be obtained:

$$\cos\gamma = \frac{1}{\sqrt{tg_\alpha^2 + tg_{\beta+1}^2}}.$$

By this formula, for changes in inclination angle of normal for each inclination angle of diffraction planes, inclination angle Ψ=β for diffraction plane may be found at which it is necessary to obtain the desired direction of normal projection on the single crystal surface, that is, solve an inverse problem: given angle α, to find angle β from angle γ. In other words, it is possible not only to conduct measurements of elastic deformation of crystal lattice of the single-crystal wafer studied with smaller number of expositions by presetting the position-sensitive detector to a calculated angle, but also to determine deformations in directions for anisotropic problem.

A number of specialists interpret elastic deformations in a single crystal as presence of stresses within crystal-bodies. This interpretation taken into account, the inventions proposed are can useful also for determination of the existence of such stresses.

Figure 5A:
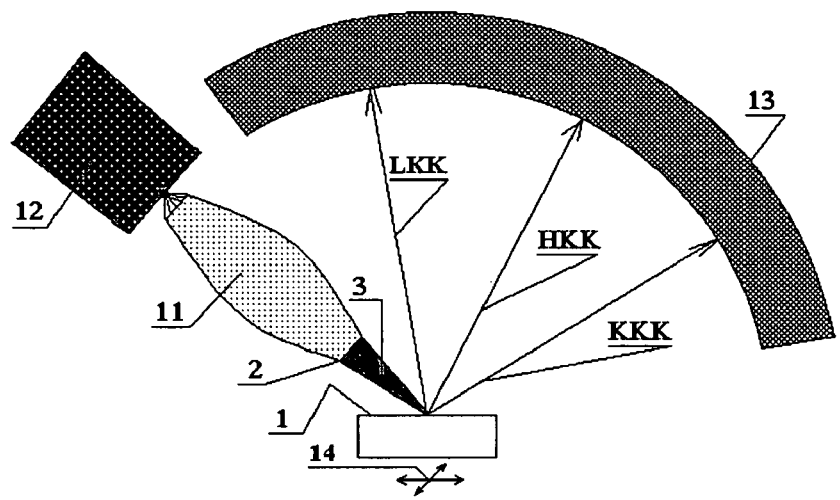
in FIG. 5a and FIG. 5b—relative arrangement of components of the device proposed for two cases of intersection point position of the converging X-ray beams with the use of single extended position-sensitive detector.
Figure 5B:
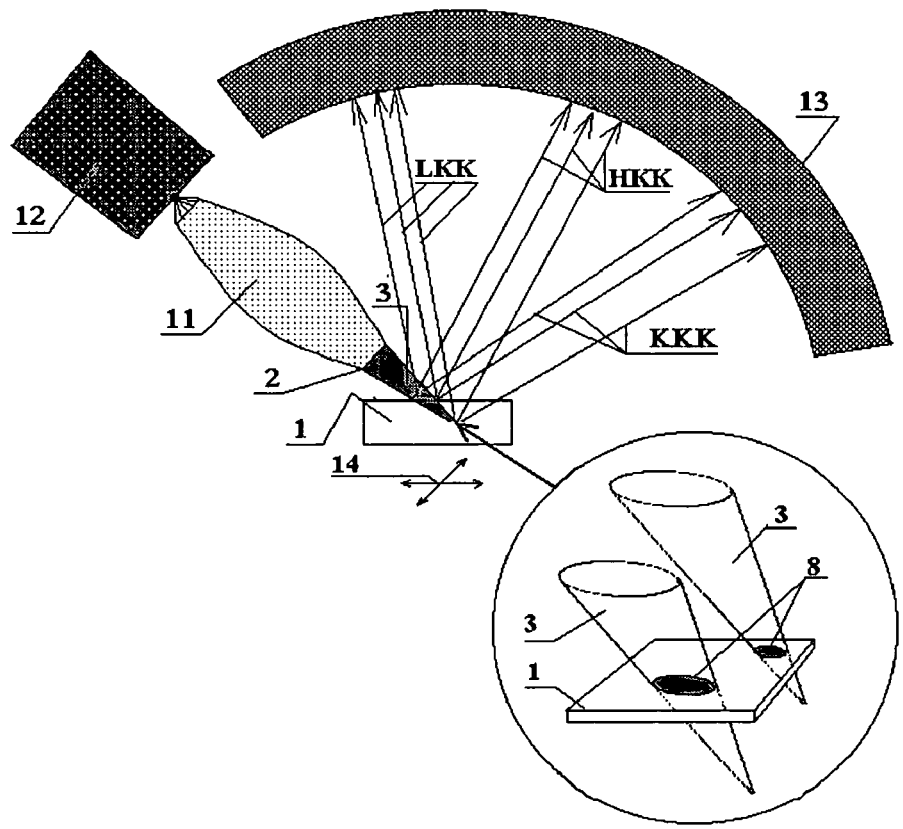

The device proposed for determination of presence of elastic stresses in single-crystal wafers (FIG. 5a) comprises X-ray tube 12, X-ray lens 11 with output end face 2 for shaping converging X-ray beam 3, two-coordinate positioning system 14 for the single-crystal wafer 1 tested and position-sensitive detector 13 or set of position-sensitive detectors, arranged on one arc opposite to expected positions of interference maxima of diffraction from the crystallographic planes studied. Means for shaping the X-ray beam acting upon single-crystal wafer inspected—X-ray lens 11—are made with possibility of forming the converging beam 3. Intersection point of rays in said beam is situated inside (below the surface) of the single-crystal wafer 1 inspected (FIG. 5a) or under said wafer. In case of said point going deep under the surface or its coming out from the side of single-crystal wafer tested opposite to that upon which the beam 3 is falling (FIG. 5b), size of irradiation zone 8 increases on the surface of wafer 1. In this case, data on elastic deformations of crystal lattice are averaged over the area inspected, with interference maxima of diffraction becoming wider, retaining coordinate for the center of gravity of maximum only at large diffraction angles. It is clear from FIG. 5b how appreciably asymmetry increases of KKK reflections relative to HKK reflections, and, even more so, to LKK reflection. Further substantial increase of the irradiation zone leads to the same errors in elastic strains control in crystal lattice of single-crystal wafer, which are inherent to the known means [2], the most close to that proposed.

Figure 6A:
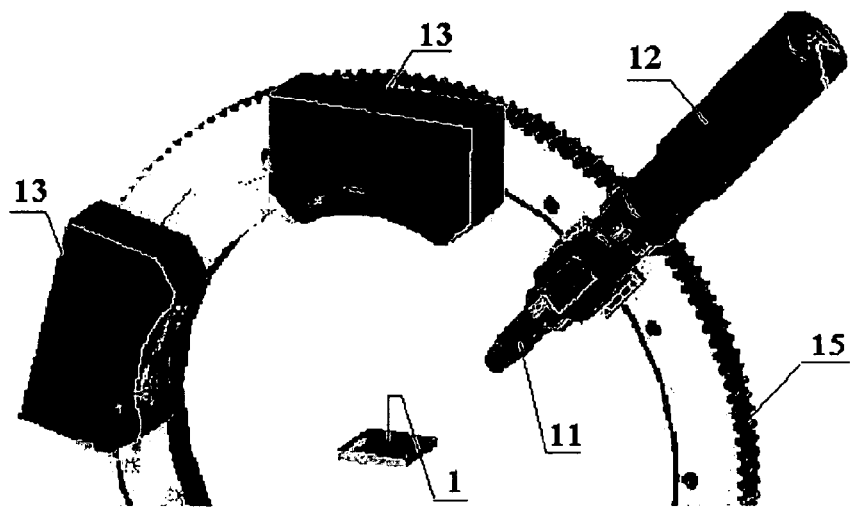
in FIG. 6a and FIG. 6b—relative arrangement of principal components of the device proposed utilizing multiple position-sensitive detectors.
Figure 6B:
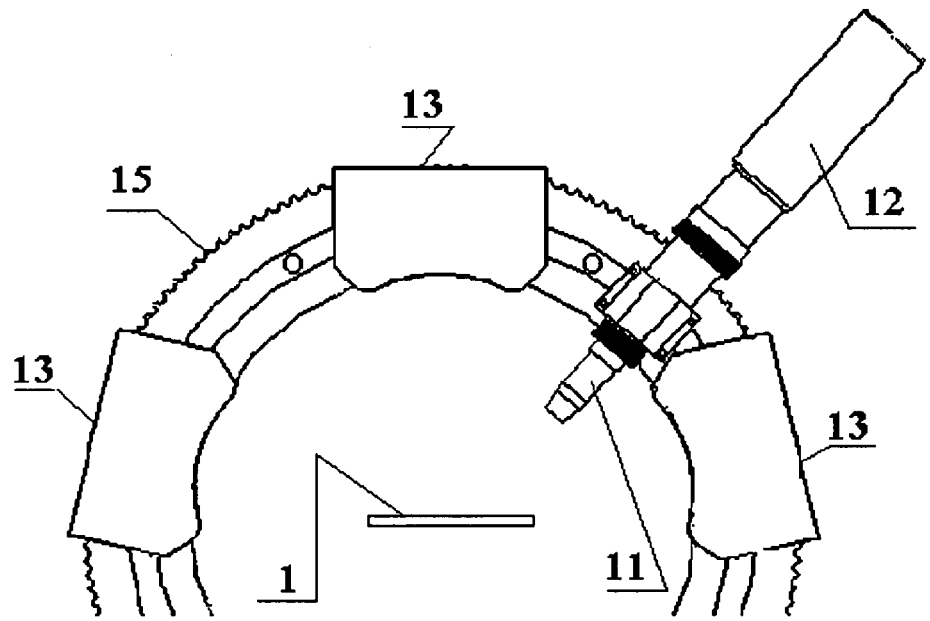

Interference maxima, corresponding to reflections from crystallographic planes of material of the single-crystal wafer tested having the form of nKK, where n may take on values H, K or L (non-equal for different selected crystallographic planes), may be detected both with two position-sensitive detectors (FIG. 6a), and with a single one having large angle of simultaneous registration. From the opposite side of X-ray tube 12 with lens 11, in case of their setting to large angles of reflection (FIG. 6b), one more position-sensitive detector 13 may be arranged. Position-sensitive detectors 13 may be arranged on the supporting arc 15 in different layouts relative to X-ray tube 12 with X-ray lens 11 and the single-crystal wafer 1 tested, depending on the research task.

All angles of mutual disorientation of nKK-type crystallographic planes are always read from the basal KKK plane of single-crystal wafer or any of nKK ones, depending on the manufacture of wafers. Error in bringing the crystallographic planes to the basal one is determined with X-ray diffractometer-comparator and entered into batch products certificate of semi-finished single-crystal wafers on the first stage of manufacture.

Process of elastic strains detection in single-crystal wafers with the device proposed may be automated. For this purpose, when using the device proposed, outputs from one or several position-sensitive detectors in said device are connected to means for the output signals processing and representation of data obtained as a result of such processing. Said means are made with possibility of determination relative position of said interference maxima and its comparison with reference values for specified system of crystallographic planes of the material of single-crystal wafer tested.

Figure 7:
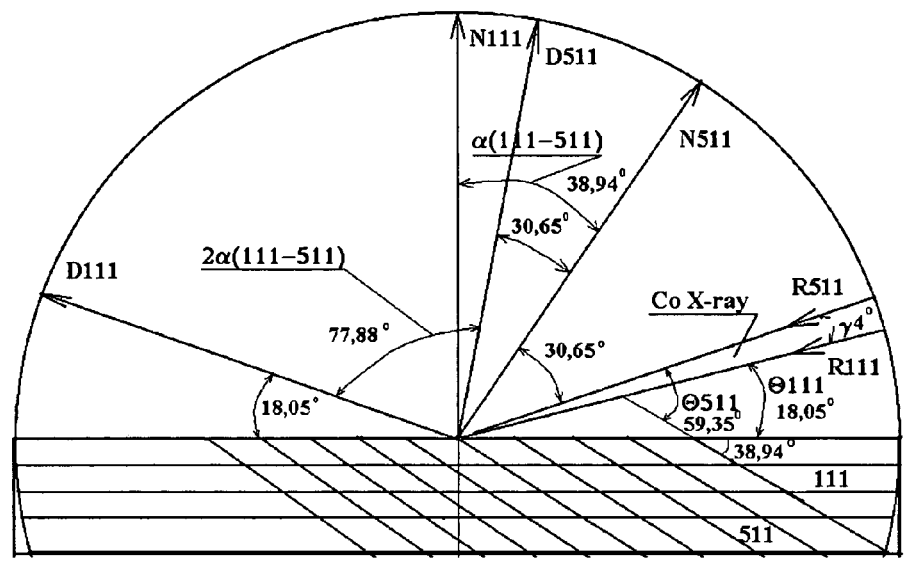
in FIG. 7 and FIG. 8—simultaneous diffraction on planes 111, 511, and planes 111, 311, correspondingly, at different convergence values of the beam acting upon single-crystal wafer.
Figure 8:
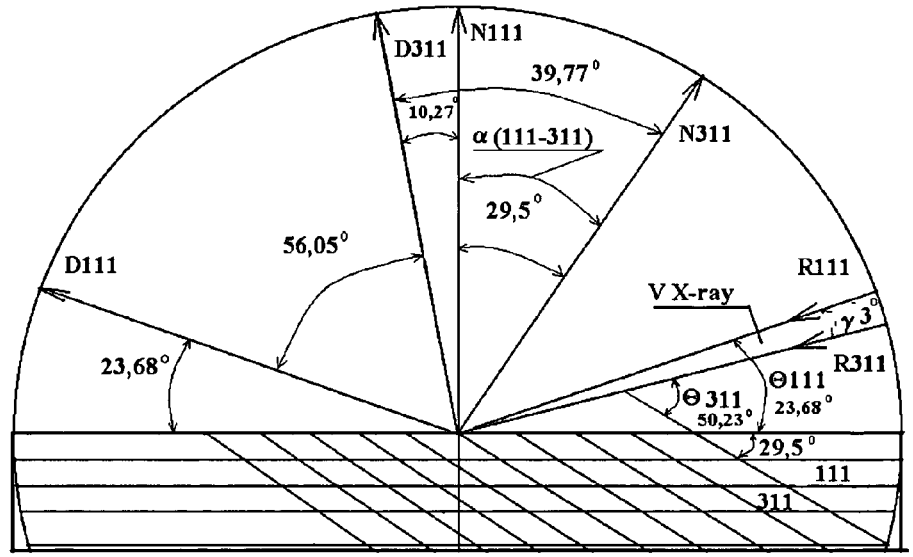

The possibility of obtaining diffraction pattern and determination of relative orientation of crystallographic planes 111, 311, 511 by centers-of-gravity shift of their interference maxima has been tested and demonstrated for silicon single-crystal wafers having basal plane 111, even if utilizing X-ray lenses with low angular convergence for X-ray tubes with cobalt anode. FIG. 7 shows simultaneous diffraction from planes 111 and 511 at angular convergence $\gamma=4°$, and FIG. 8—simultaneous diffraction from planes 111 and 311 at angular convergence $\gamma=3°$ for X-ray tubes with vanadium anode. By using X-ray lens with angular convergence $\gamma=8°$ for silicon single-crystal wafer, the conditions may be satisfied of simultaneous diffraction for planes 111, 311, 511.

These same conditions of simultaneous diffraction from planes 111, 311 and 511 for silicon single-crystal wafers may be satisfied also when using X-ray lens with angular convergence $\gamma$ below 5°. To do this requires use of X-ray tube with mixed Co-V anode. Then two $K_\alpha$ wavelengths present in primary X-ray beam—Co and V series—make it possible not only to obtain simultaneous interference diffraction pattern from said planes, but also obtain it at two different wavelengths. This is of particular importance, because presence of simultaneous reflections from crystallographic planes 111 in cobalt and vanadium radiation provides the most accurate natural reference for angular measurements of all other quantities. Interference maxima don't overlap and reflect in Co $K_\alpha$ radiation planes 111 and 511, and in V $K_\alpha$ radiations—planes 111 and 311.

In experiments with 10 W X-ray tube and X-ray lenses having abovementioned values of convergence angle for the beam formed, determination of centers-of-gravity for interference maxima has been achieved with error of 12 second of angle at exposure time below 20 seconds.

PRIOR ART DOCUMENTS

1. Y. Kawano et al. Infra Red System GaAs/AlGaAs., J. Appl. Phys. 2001, 89, p. 4037.
2. O. Brümmer. Zeitschrift für Naturforschungen, 15A, S.875, 1960.
3. U.S. Pat. No. 5,192,869, publ. Sep. 3, 1993.

The invention claimed is:

1. Method for determination of elastic strain present in single-crystal wafers, in which a tested single-crystal wafer is illuminated with an X-ray beam, registration of an interference pattern of diffraction is performed, and relative position of interference maxima is determined and used to judge the presence of elastic strain, wherein:
   the single-crystal wafer is illuminated with a converging X-ray beam having a point of ray intersection inside said single-crystal wafer or on a side opposite to that on which said converging X-ray beam falls, said converging X-ray beam has angular convergence sufficient for providing diffraction conditions simultaneously for multiple crystallographic planes; and
   the determination of relative position of the interference maxima is performed for diffraction reflections from crystallographic planes having different indices of the form of nKK, where n is equal to H, K, or L and differs for distinct crystallographic planes, by utilizing one or several position-sensitive X-ray detectors.

2. Method according to claim 1, wherein He shaping of the converging X-ray beam is achieved by using an X-ray focusing lens.

3. Device for determination of elastic strain present in single-crystal wafers, comprising:
   means for positioning a tested single-crystal wafer,
   an X-ray emitter having means for shaping an X-ray beam directed on the tested single-crystal wafer, and
   means for registration of an interference pattern of diffraction,
   wherein the means for shaping the X-ray beam forms a converging beam so as to have a point of ray intersection of the converging beam inside the single-crystal wafer or on a side opposite to that on which said beam falls,
   said converging beam has angular convergence sufficient for providing simultaneous diffraction for multiple crystallographic planes, and
   said means for registration comprises one or several position-sensitive X-ray detectors for receiving diffracted radiation in the whole angular range containing interference maxima corresponding to reflections from crystallographic planes of material of the single-crystal wafer having different indices of the form of nKK, where n is equal to H, K, or L and differs for distinct crystallographic planes.

4. Device according to claim 3, wherein said means for shaping the X-ray beam is a focusing X-ray lens.

* * * * *